United States Patent
Zheng et al.

(10) Patent No.: US 10,864,456 B2
(45) Date of Patent: *Dec. 15, 2020

(54) SYSTEM AND METHOD TO PARTIALLY VAPORIZE A PROCESS STREAM BY MIXING THE STREAM WITH A HEATING MEDIUM

(71) Applicant: Cameron Solutions, Inc., Houston, TX (US)

(72) Inventors: Z. Frank Zheng, Cypress, TX (US); Christopher Stephen King, Houston, TX (US); Harihara V. Nemmara, Katy, TX (US)

(73) Assignee: CAMERON SOLUTIONS, INC., Houston, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 16/413,828

(22) Filed: May 16, 2019

(65) Prior Publication Data
US 2019/0270030 A1    Sep. 5, 2019

Related U.S. Application Data

(63) Continuation of application No. 15/193,839, filed on Jun. 27, 2016, now Pat. No. 10,328,360.

(51) Int. Cl.
*C02F 1/10* (2006.01)
*B01D 1/00* (2006.01)
(Continued)

(52) U.S. Cl.
CPC ......... *B01D 1/0041* (2013.01); *B01D 1/0064* (2013.01); *B01D 1/0094* (2013.01);
(Continued)

(58) Field of Classification Search
None
See application file for complete search history.

(56) References Cited

U.S. PATENT DOCUMENTS 3,181,600 A    5/1965  Woodward et al.
3,294,649 A    12/1966 Powell, Jr.
(Continued)

FOREIGN PATENT DOCUMENTS

DE    2346609 A1    3/1975
GB    1262458 A     2/1972
WO    2007073204 A1  6/2007

OTHER PUBLICATIONS

Gamble, G, et al., Optimizing heat transfer fluid performance, 2014, Eastman Chemical Company, p. 8. (Year: 2014).*
(Continued)

*Primary Examiner* — Derek N Mueller
(74) *Attorney, Agent, or Firm* — Hauptman Ham, LLP; Ronald G. Embry, Jr.

(57) ABSTRACT

A system and method to partially vaporize a process or feed water stream does so in a liquid pool zone of a vessel as the stream comes into contact with a heating medium that is less volatile than the process stream. To keep the pool hot, the heating medium can be recirculated through a heater of a pump-around loop or a heater can be placed in the liquid pool. As the process stream is partially vaporized, any solids present in the process stream together with the unvaporized process or feed water stream move into the heating medium. These solids and unvaporized liquids may be further removed from the heating medium in the pool or in the
(Continued)

pump-around loop. The vaporized process stream can be further condensed. Any heat recovered can be used to pre-heat the process stream or in the pump-around loop's heater in case of mechanical vapor recovery.

18 Claims, 3 Drawing Sheets

(51) Int. Cl.
  *B01D 5/00* (2006.01)
  *B01D 1/14* (2006.01)
  *B01D 1/28* (2006.01)
  *C07C 29/76* (2006.01)
  *C02F 103/08* (2006.01)
(52) U.S. Cl.
  CPC .............. *B01D 1/14* (2013.01); *B01D 1/2856* (2013.01); *B01D 5/006* (2013.01); *C02F 1/10* (2013.01); *C07C 29/76* (2013.01); *C02F 2103/08* (2013.01); *Y02P 20/123* (2015.11); *Y02P 20/57* (2015.11); *Y02P 70/34* (2015.11)

(56) References Cited

U.S. PATENT DOCUMENTS 3,875,019 A * 4/1975 Cocuzza .............. B01D 53/263
                                                       203/18
8,652,304 B2    2/2014 Nazzer

OTHER PUBLICATIONS

Perry's Chemical Engineer's Handbook, 2008, 8th ed., McGraw-Hill, p. 13-5.
GE, Water and Process Technology, 2012, (retrieved Mar. 30, 2018).
Detlef Gille, Seawater intakes for desalination plants, 2003, Desalination, vol. 156, pp. 249-256.
International Search Report and Written Opinion issued in the PCT Application PCT/US2017/039490, dated Sep. 11, 2017 (14 pages).
International Preliminary Report on Patentability issued in the PCT Application PCT/US2017/039490, dated Jan. 1, 2019 (8 pages).
Office Action issued in the EP Application 17748962.2, dated Nov. 25, 2019 (6 pages).
Search report and Written Opinion issued in the SG application 11201811598Y, dated Mar. 13, 2020 (8 pages).

* cited by examiner

SYSTEM AND METHOD TO PARTIALLY VAPORIZE A PROCESS STREAM BY MIXING THE STREAM WITH A HEATING MEDIUM

RELATED APPLICATIONS

The present application claims priority from U.S. application Ser. No. 15/193,839, filed Jun. 27, 2016, the disclosure of which is hereby incorporated by reference herein in its entirety.

BACKGROUND

This disclosure is in the field of vaporization and desalination processes such as, but not limited to, those used in mono ethylene glycol ("MEG") reclamation applications, seawater desalination applications, total dissolved solids reduction applications, and general process water treatment for reuse or disposal.

Current vaporization and desalination processes are complicated, expensive, and typically require extensive pretreatment. In some cases, the cost of pretreatment exceeds the cost of the actual vaporization or desalination processes. U.S. Pat. No. 8,652,304 B2 ("Nazzer") discloses a method of extracting dissolved or undissolved solids from a mixture of water and a process liquid or stream. The mixture is introduced into a mixing zone within or upstream of a separation vessel where it is further mixed with a recycle fluid extracted from a liquid pool zone of the separator vessel and pumped through a heat exchanger.

Vaporization occurs in this mixing zone (where more than 99% of the volatile components of the feed stream are vaporized). The resulting stream is then transferred to the separator vessel in which the vapor is separated, with the solid and liquid components falling into the liquid pool zone of the separator vessel. A portion of these solids and liquids that bond to these solids then passes through a stripping zone of the separator vessel. Water residing within the stripping zone displaces the liquids bound to the solids and an aqueous waste stream with dissolved or nondissolved solids results.

Because this method requires a mixing zone for vaporization outside of the liquid pool, the required equipment is difficult to design and prone to scaling and plugging. The method also does not allow for vaporization within the liquid pool and requires the heating medium—i.e., the recycle fluid, lighter than the water in the stripping zone—to be recycled at a rate of at least ten times that of the process feed rate. This high recycle rate is required because the method must limit the temperature difference between the recycle fluid and the process stream in order to avoid thermal degradation effects. Additionally, the method does not allow for partial vaporization with a blowdown.

Last, the method requires a stripping zone for solids removal. A stripping zone is prone to corrosion because of unvaporized (solids) components from the process stream. The stripping zone also presents safety concerns due to the risk of higher temperature oil contacting water. To reduce the safety concern, the oil must be cooled before it touches the water in the stripping zone, but cooling the oil increases its viscosity and ineffective solids separation results. The stripping zone does not allow for partial vaporization because partial vaporization can bring an extensive amount of unvaporized process liquid into the stripping zone.

SUMMARY

The present disclosure allows partial vaporization to occur, simplifies the system and method of vaporizing a process (or feed water) stream, and reduces the cost of doing so.

Vaporization in a mixing zone outside of the liquid pool does not occur in embodiments of the system and method, nor do the system and method have a stripping zone for solids removal. The system and method is not limited to a light heating medium relative to the process stream. Any pre-mixing of the process stream and heating medium may be done at a level below that required for partial vaporization of the process or feed water stream. Pre-mixing may also be done to provide a relatively small amount of vaporization to enhance the pre-mixing and accelerate the fluid when it enters the liquid pool.

Embodiments of the system and method may disperse the process or feed water stream into a liquid pool containing a hot heating medium that is less volatile than, and immiscible with, the process or feed water stream. To keep the pool hot, the heating medium can be recirculated through a heater in a pump-around loop. Alternatively or additionally, a heater can be placed in the liquid pool.

As the process stream is partially vaporized, any dissolved or undissolved solids present in the process or feed water stream come out of the stream together with the unvaporized process or feed water stream and move into the heating medium. The solids and unvaporized process stream or feed water that move into the heating medium may be further removed from the heating medium within the vessel or in a separator located in the pump-around loop. If the removal of solids and unvaporized liquids occurs in the vessel, the vessel should include internals of a kind known in the art to the separate the unvaporized portion of the process or feed water stream from the heating medium. If the removal of the solids and unvaporized liquids occurs in a separator in the pump-around loop, the separator can be a hydrocyclone, centrifuge, particulate filter, settling tank, or some other piece of separation device equivalent to these.

In some embodiments, the vaporized process or water stream can be condensed or compressed and condensed. Heat recovered during condensing can be used to pre-heat the process stream prior to its introduction into the liquid pool, or to heat the heating medium in the pump-around loop.

The system and method can be used in applications such as but not limited to MEG reclamation; seawater desalination; steam generation; total dissolved solids ("TDS") reduction for produced water, desalter wash water, fracking flowback water, and amine reclamation. Unlike prior art systems and methods, there is no pretreatment of the process or feed water stream or low temperature differentials between the vaporization temperature of the stream and heating medium (e.g., limited to 10° C. above the vaporization temperature due to the risk of scaling in the heat exchanger in the pump-around loop).

The embodiments of this disclosure may simplify the system and method to partially vaporize a process stream; reduce the costs associated with prior art partial vaporization systems and processes; eliminate the design and operational challenges presented by mixing zones located outside of the liquid pool zone of the vessel and stripping zones for solids and unvaporized process stream or feed water removal; and eliminate the prior art's limitation of not being able to be used in partial vaporization applications in which a portion of the unvaporized process or feed water stream remains in liquid form. The disclosure eliminates the need for light heating mediums relative to the process or feed water stream. The disclosure also does not require the low temperature differential between the stream and heating medium or recycle rates of at least 10 times greater than that of the process feed.

The disclosure also reduces, and potentially eliminates, pretreatment for the process or feed water stream while at the same time minimizing or eliminating scaling and fouling of equipment. Any pre-mixing of the process or feed water stream and the heating medium that occurs outside of the liquid pool zone may be done at a level below that at which the stream partially vaporizes. Pre-mixing may also be done to provide a relatively small amount of vaporization to enhance the pre-mixing and accelerate the fluid when it enters the liquid pool.

BRIEF DESCRIPTION OF THE DRAWINGS

So that the above recited features can be understood in detail, a more particular description may be had by reference to embodiments, some of which are illustrated in the appended drawings, wherein like reference numerals denote like elements. It is to be noted, however, that the appended drawings illustrate various embodiments and are therefore not to be considered limiting of its scope, and may admit to other equally effective embodiments.

ELEMENTS AND NUMBERING USED IN THE DRAWINGS AND DETAILED DESCRIPTION

Figure 1:
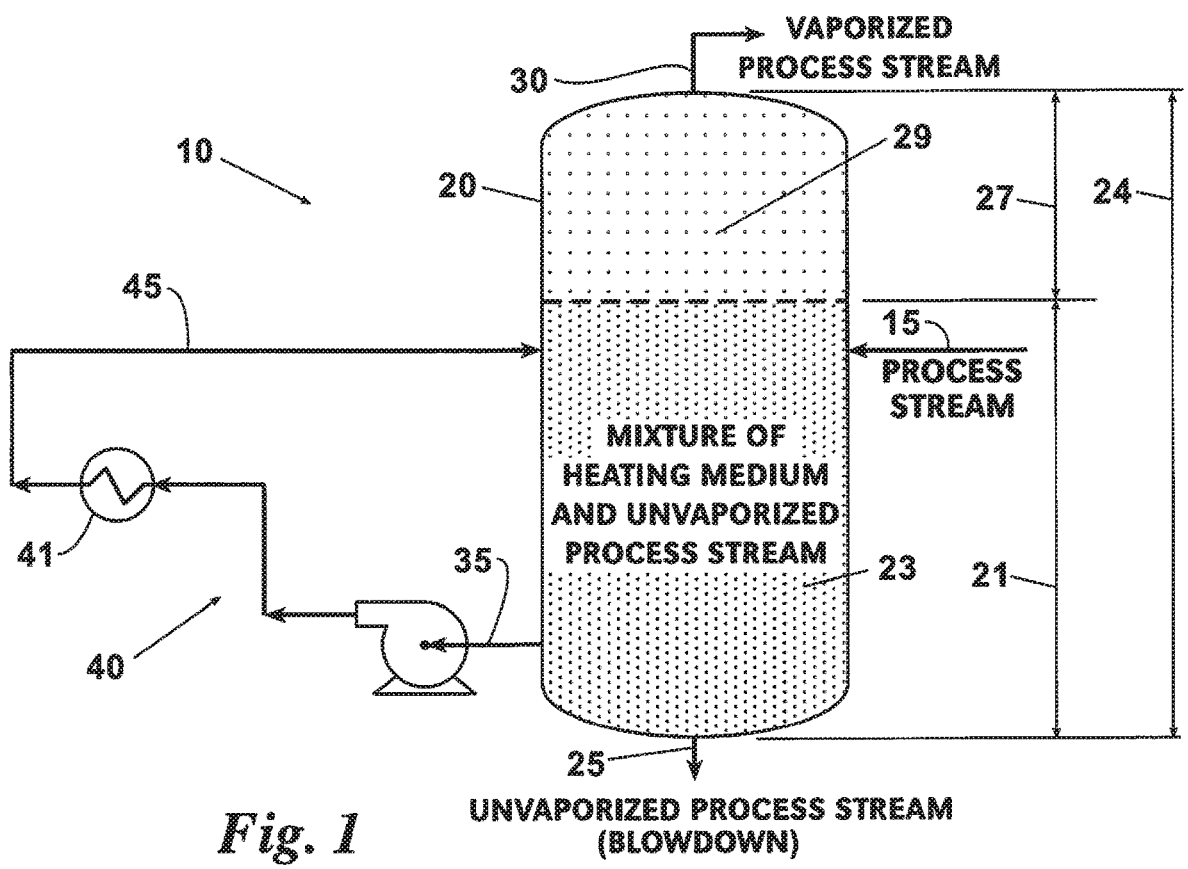
FIG. 1 is an embodiment of a system and method to partially vaporize a process or feed water stream. A process stream having dissolved or undissolved solids is routed to a heating medium pool of a vessel. As the process stream partially vaporizes, dissolved solids may reach saturation and turn to undissolved solids. The unvaporized portion of the process stream, including both solids and unvaporized liquids, moves into the heating medium. The vessel includes internals to allow the separation of the unvaporized portion of the process stream from the heating medium and remove the unvaporized portion of the process stream out of the vessel. A pump-around loop recycles and heats the heating medium. If any pre-mixing of the process stream and heating medium occurs outside of the liquid pool (see FIG. 6), the pre-mixing may be at a level below that at which vaporization occurs. Pre-mixing may also be done to provide a relatively small amount of vaporization to enhance the pre-mixing and accelerate the fluid when it enters the liquid pool.
Figure 2:
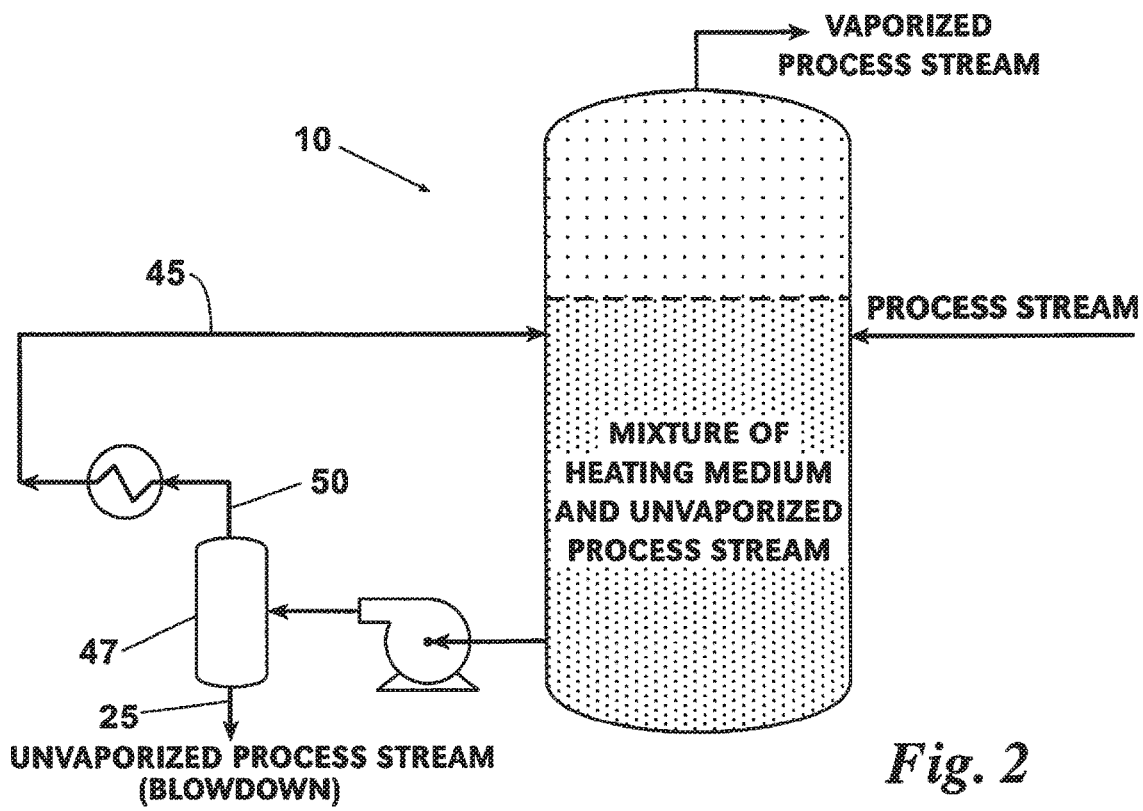
FIG. 2 is an embodiment of the system and method. The pump-around loop includes a separator for removing solids alone or in combination with unvaporized liquid components of the process stream. The separator can be a hydrocyclone, centrifuge, particulate filter, settling tank, or some other piece of separation device equivalent to these.

10 System or method
15 Process (or feed water) stream
15A Process stream prior to preheating
15B Pre-heated process stream
17 Mixer within or outside of 20
20 Vessel
21 Liquid pool zone
23 Heating medium
24 Interior volume
25 Unvaporized (dissolved and undissolved solids and unvaporized liquids) portion of 15
27 Vapor separation zone
29 Vaporized volatile components of 15
30 Vaporized process stream
35 Removed heating medium stream or mixture (heating medium 23 and portion of 25)
40 Pump-around loop
41 Heater
45 Heated recycle stream substantially unvaporized portion-free or with a reduced unvaporized portion 25 (relative to removed stream or mixture 35)
47 Separator or separator device (such as a hydrocyclone, centrifuge, particulate filter, settling tank or their equivalents)
50 Heating medium stream substantially unvaporized portion-free or with a reduced unvaporized portion 25 (relative to removed stream or mixture 35)
60 Condenser
65 Partially or totally condensed process stream
70 Compressor
75 Pressurized stream

DETAILED DESCRIPTION

In the following description, numerous details are set forth to provide an understanding of some embodiments of the present disclosure. However, it will be understood by those of ordinary skill in the art that the system and/or methodology may be practiced without these details and that numerous variations or modifications from the described embodiments may be possible.

In the specification and appended claims, the terms "connect", "connection", "connected", "in connection with", and "connecting" are used to mean "in direct connect with" or "in connection with via one or more elements"; and the term "set" is used to mean "one element" or "more than one element". Further, the terms "couple", "coupling", "coupled", "coupled together", and "coupled with" are used to mean "directly coupled together" or "coupled together via one or more elements". As used herein, the terms "up" and "down", "upper" and "lower", "upwardly" and "downwardly", "upstream" and "downstream", "above" and "below", and other like terms indicated relative positions above or below a given point or element and are used in this description to more clearly describe some embodiments of the disclosure.

Embodiments of a system and method to partially vaporize volatile components of a process or feed water stream achieve partial vaporization of those components in the liquid pool zone of the vessel when the stream contacts a heating medium residing in the liquid pool zone. The vessel is arranged to directly receive the process or feed water stream, thereby eliminating pre-treatment between it and the upstream process providing the stream. A pump-around loop heats a portion of the heating medium and recycles this heated portion back to the vessel.

The heating medium—which is immiscible with the stream and can be lighter or heavier than the stream—is maintained at an operating temperature required for the desired partial vaporization effects. Pre-mixing may also be done to provide a relatively small amount of vaporization to enhance the pre-mixing and accelerate the fluid when it enters the liquid pool. The vessel can also make use of blowdown to remove solids formed during the vaporization of the process or feed water stream. Blowdown, as used here, refers to the removal of the unvaporized process (or feed water) stream with concentrated levels of dissolved or undissolved solids. A separate vessel located in the pump-around loop can be used for the separation of the blowdown.

The different arrangements of the system and method 10 as shown in FIGS. 1 to 6 route a process or feed water stream 15 into a vessel 20 whose interior volume 24 is defined by a liquid pool zone 21 and a vapor separation zone 27. A heating medium 23 resides within the liquid pool zone 21 and this heating medium 23 is used to partially vaporize the volatile components 29 of the process stream 15. Mixing of the process stream 15 and heating medium 23 occurs naturally within the liquid pool zone 21 as the process stream 15 enters the zone 21.

Figure 3:
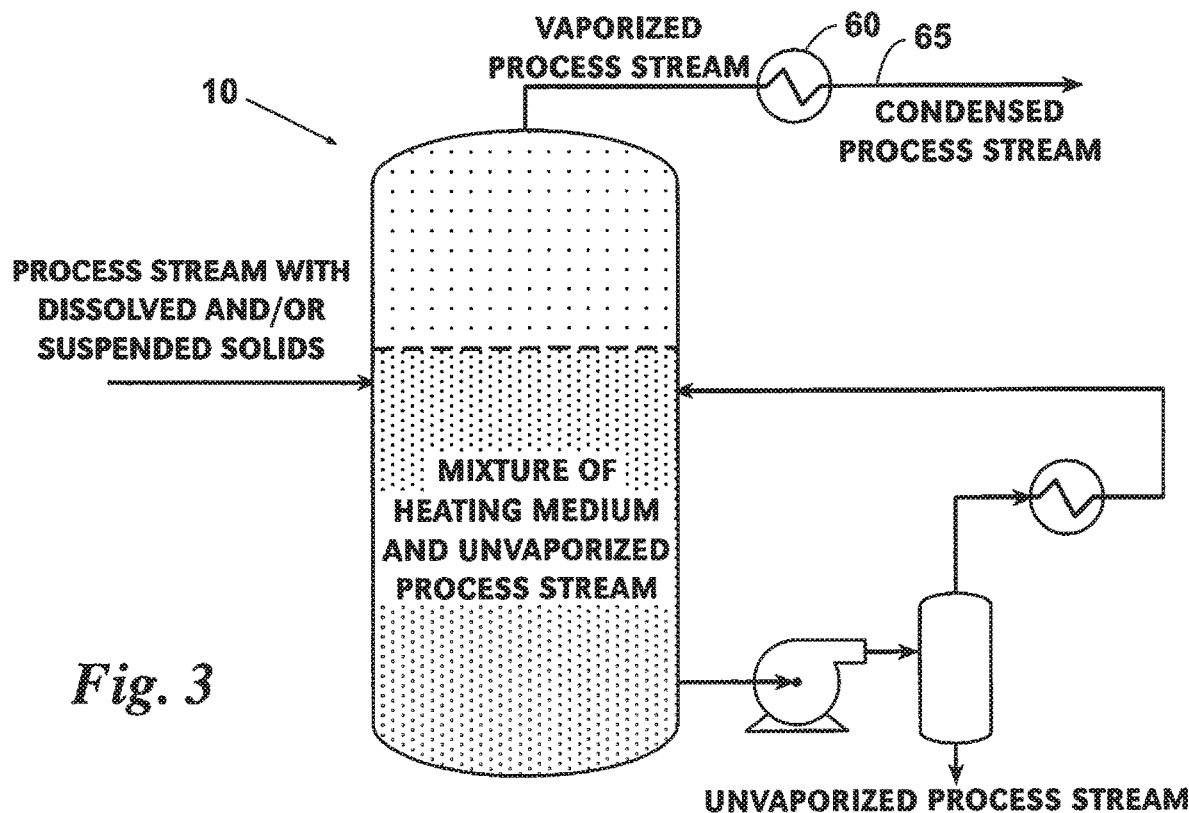
FIG. 3 is an embodiment of the system and method. The vaporized process stream is partially condensed.
Figure 4:
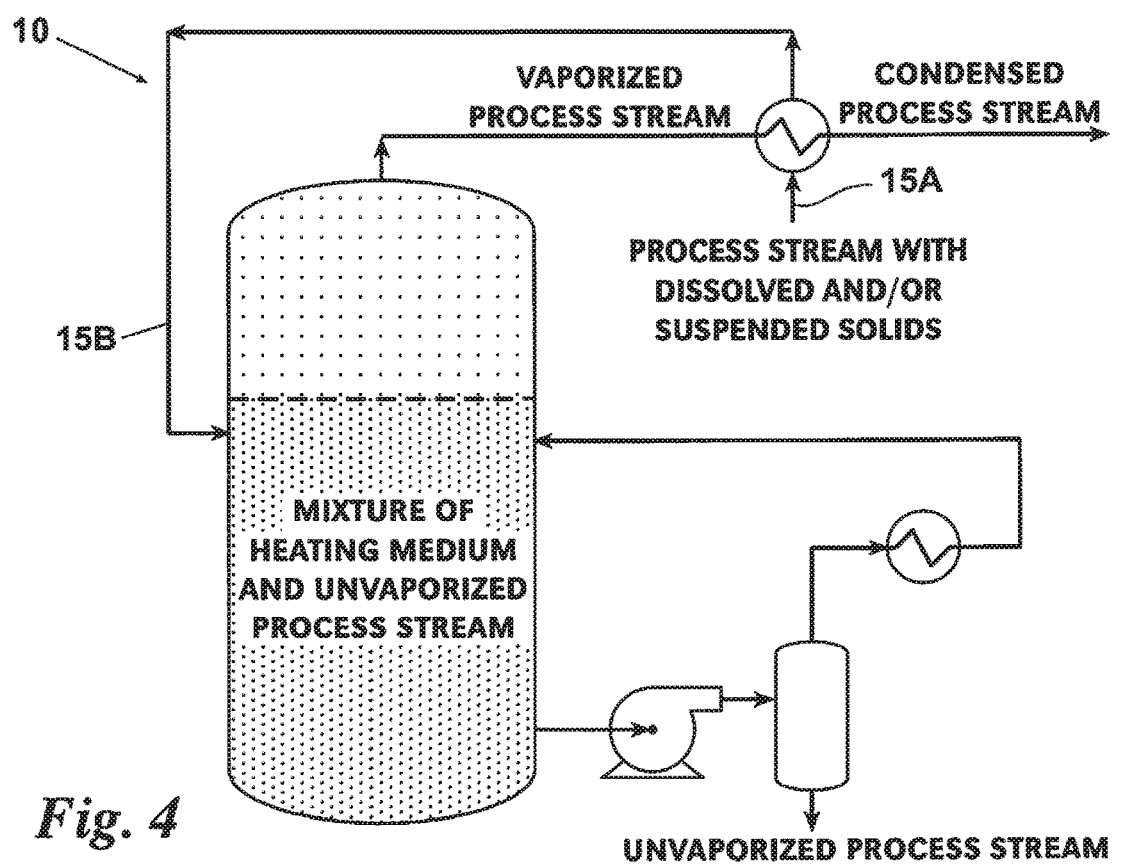
FIG. 4 is an embodiment of the system and method. Heat recovered from condensing is used to pre-heat the process stream prior to it being routed to the heating medium pool of the vessel.

The now vaporized portions 29 of the process stream 15 migrate to a vapor separation zone 27 of the vessel 20 and are removed as a vaporized process stream 30. The vaporized process stream 30 can be routed to a condenser 60, as shown in FIGS. 3 and 4, to produce a partially condensed process stream 65. Heat from the condenser 60 can be recovered and used to raise the temperature of the process stream 15A so that stream 15 flows into the liquid pool zone 21 as a pre-heated process stream 15B.

Figure 5:
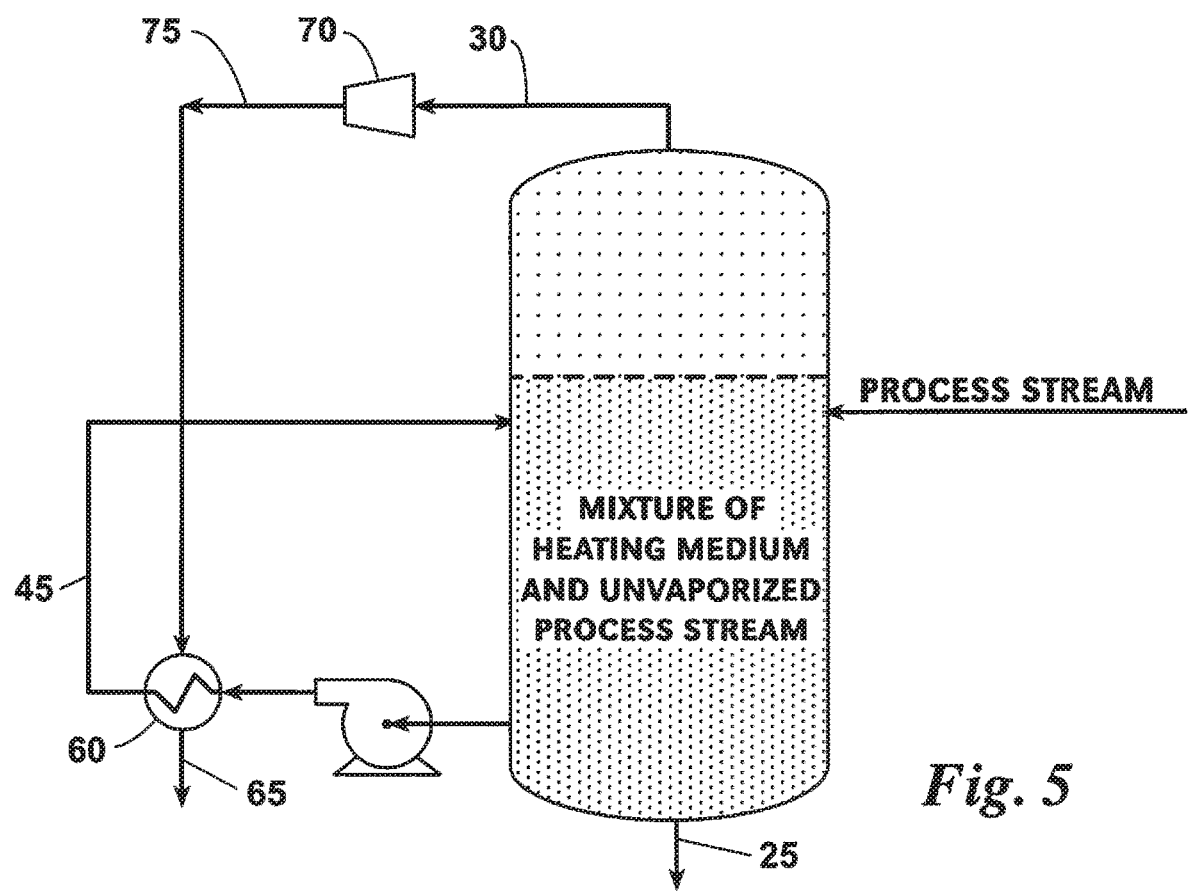
FIG. 5 is an embodiment of the system and method. The vaporized process stream is compressed and this pressurized process stream is condensed in the pump-around loop to help heat the heating medium being recycled in the loop.
Figure 6:
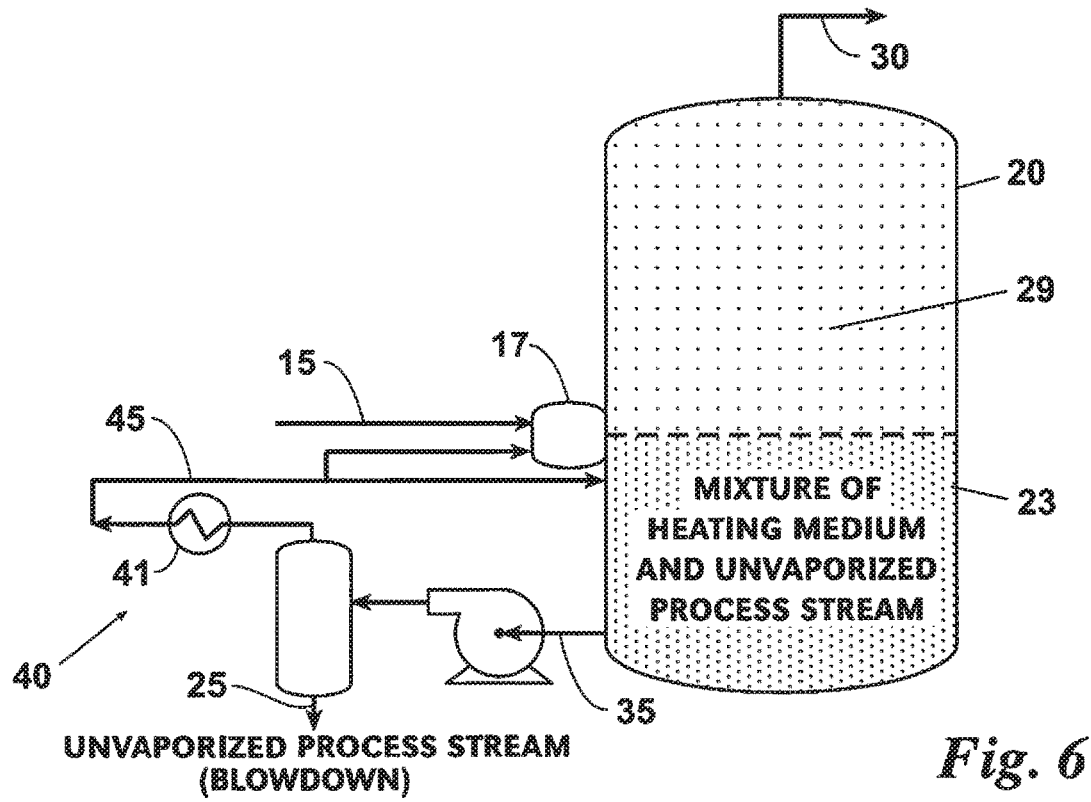
FIG. 6 is an embodiment of the system and method. Pre-mixing of the process stream and heating medium occurs outside of the liquid pool zone of the vessel but at a level below that needed for vaporization. Pre-mixing may also be done to provide a relatively small amount of vaporization to enhance the pre-mixing and accelerate the fluid when it enters the liquid pool

The vaporized process stream 30 can also be routed to a compressor 70, as shown in FIG. 5. The now pressurized process stream 75 is condensed in the pump-around loop 40, with heat being recovered and used to heat the recycle stream 45.

As the volatile components 29 of the process stream 15 vaporize, the unvaporized portion 25 of the process stream 15 moves into the liquid pool zone 21 along with the heating medium 23. Because the unvaporized portion 25 is immiscible with the heating medium 23, that portion can separate from the heating medium 23 in the vessel 20 or within a separator 47 located in the pump-around loop 40. The unvaporized portion 25, both liquid and undissolved solids, can be removed as blowdown stream 25. No stripping zone is used.

The separator 47 used in the pump-around loop 40 can be any separator suitable, including but not limited to a hydrocyclone, centrifuge, particulate filter, settling tank, or some other piece of separation device equivalent to these. A heating medium stream 50 with reduced amounts of, or without, unvaporized solids and liquids 25 exits the separator 47 and passes through the heater 41. The heated recycle stream 45 then recycles back to the liquid pool zone 21 of the vessel 20. The heated recycle stream 45 may include some portion of the unvaporized solids and liquids 25 of the process stream 15.

The heating medium 23 is maintained at an operating temperature that provides the desired vaporization effects. The heating medium 23 can be any heating medium depending on the make-up of process or feed water stream 15 and application-specific requirements. For example, the heating medium 23 could be one that one that is lighter than or heavier than the process stream 15. However, the heating medium 23 is immiscible with the process stream 15 to form a heterogeneous mixture with the process stream 15. The heating medium 23 is also less volatile than the volatile components 29 of the process stream 15.

To keep the heating medium 23 at the selected operating temperature, a heater (not shown) can be placed in the liquid pool zone 21. Alternatively or additionally, a removed stream 35 of the heating medium 23, which may include solids and unvaporized liquids 25 residing within the liquid pool zone 21, can be removed from the vessel 20 and routed to the pump-around loop 40 and its heater 41. A heated recycle stream 45, that may include dissolved and undissolved solids and unvaporized liquids 25, then recycles back to the liquid pool zone 21.

An embodiment of a method to partially vaporize a process stream includes:

routing the process (or feed water) stream 15 directly into the liquid pool zone 21 of the vessel 20 where it becomes mixed with a heating medium 23 that is less volatile than the process stream 15 and maintained at an operating temperature determined by vaporization requirements to partially vaporize a volatile components portion 29 of the process stream 15; and removing the vaporized portion 29 of the process stream 15 from the vapor separation zone 27 of the vessel 20 as a vaporized process stream 30.

Prior to the process stream 15 entering the liquid pool zone 21 there may be no pre-treatment of the stream 15 as it exits the upstream process providing the stream 15 and there may be no mixing of the process stream 15 with the heating medium 23. Pretreatment means treatment such as but not limited to chemical dosing, filtration using selectively permeable membranes, separators, or the use of ion exchange, deaerators or blowdown prior to the process stream 15 entering vessel 20 (or some combination of the above pretreatment methods). (Coarse straining of a kind known in the art and typically done ahead of pretreatment might be used if the feed is taken directly from a natural body of water or from a source with excessive undissolved solids.) If any pre-mixing of the process stream 15 and heating medium 23 occurs outside of the liquid pool zone 21 (see e.g. mixer 17 in FIG. 6), the pre-mixing may be done at a level below that at which vaporization occurs. Therefore, partial vaporization of the process stream 15 occurs within the liquid pool zone 21 of the vessel 20.

Pre-mixing may also be done to provide a relatively small amount of vaporization to enhance the pre-mixing and accelerate the fluid 15, 45 when it enters the liquid pool 21. The amount of vaporization that occurs in pre-mixing may be less than that which occurs in the liquid pool 21. For example, during normal (non-turndown) operations no more than about 20% or about 5% of the volatile components in the stream 15 may vaporize during pre-mixing. If the amount of vaporization does exceed that of the liquid pool, during normal operations vaporization during pre-mixing should not exceed about 80% or about 90% of the volatile components. Limiting the amount of vaporization during pre-mixing helps avoid the design challenges and scaling and plugging problems associated with the mixing zone of the prior art (see Background).

The heating medium 23 and process stream 15 form a heterogeneous mixture when residing within the liquid pool zone 21. Additionally, the density of the heating medium 23 can be greater than or less than that of the process stream 15.

The method can also include removing a portion 35 of the heating medium 23 residing in the liquid pool zone 21 of the vessel 20; raising a temperature of the removed portion or stream 35 to produce a heated recycle stream 45; and routing the heated recycle stream 45 back to the liquid pool zone 21. The removed stream 35 can also be routed to a separator 47 to produce heating medium stream 50 substantially unvaporized portion-free or with a reduced unvaporized portion 25. Once stream 50 is heated by heater 41, it can be returned to the liquid pool zone 21 as the heated recycled stream 45 (also substantially unvaporized portion-free or with a reduced unvaporized portion 25).

The method can also include condensing at least a portion of the vaporized process stream 30. Heat recovered from the condenser 60 can be used as pre-heating to raise the temperature of at least a portion of the process stream 15A prior to the process stream 15B entering the liquid pool zone 21 of the vessel 20. Alternatively or additionally, the method can include compressing at least a portion of the vaporized process steam 30. The pressurized stream 75 is then condensed in the pump-around loop 40 and used to raise the temperature of the recycle stream 45.

An embodiment of a system to partially vaporize a process stream includes a vessel 20 arranged to contact a process or feed water stream 15 exiting an upstream process and route the process stream 15 into a heating medium 23 residing within the liquid pool zone 21 of the vessel 20. The interior volume 24 of the vessel 20 does not include a stripping zone for solids and liquids 25 removal. The heating medium 23 is less volatile than the process stream 15 and maintained at an operating temperature determined by vaporization requirements. The partially vaporized volatile components 29 of the process stream 15 migrate to the vapor separation zone 27 of the vessel 20.

A pump-around loop 40 is arranged to receive a portion 35 of the mixed heating medium 23 along with the non-volatile (dissolved and undissolved) components and unvaporized liquids 25 of the process stream 15 that have moved into the heating medium 23 and then return the portion 35 back to the liquid pool zone 21 as a heated recycle stream 45. The pump-around loop 40 of the system can also include a heater 41 as well as a separator 47 arranged upstream of the heater 41 so that a substantially unvaporized portion-free or reduced unvaporized portion heating medium stream 45 is being returned to the vessel 20.

Prior to contacting the heating medium 23, the process stream 15 may not be mixed with the heating medium 23 outside of the liquid pool zone 21 of the vessel 20. If any pre-mixing of the stream 15 and heating medium 23 occurs, the mixing may be at a level below that required for vaporization of the volatile components 29. Pre-mixing may also be done to provide a relatively small amount of vaporization to enhance the pre-mixing and accelerate the fluid when it enters the liquid pool 21.

The system can also include a condenser 60 arranged to receive at least a portion of a vaporized process stream 30 exiting the vapor separation zone 27 of the vessel 20. Heat recovered from the condenser 60 can also serve as a pre-heater to raises the temperature of the process stream 15A prior to the process stream 15B directly entering the liquid pool zone 21 of the vessel 20.

Alternatively or additionally, the system can include a compressor 70 arranged to receive at least a portion of the vaporized process stream 30. Heat recovered from condensing the pressurized stream 75 can be used in the pump-around loop 40 to raise the temperature of the recycle stream 45.

Although the preceding description has been described herein with reference to particular means, materials, and embodiments, it is not intended to be limited to the particulars disclosed herein; rather, it extends to all functionally equivalent structures, methods, and uses, such as are within the scope of the appended claims.

What is claimed:

1. A method to partially vaporize a process stream, the method comprising:
   routing the process stream into a liquid zone of a vessel, the liquid zone including a heating medium that is less volatile than the process stream, immiscible with the process stream, and maintained at a vaporization operating temperature;
   providing a mixture of the process stream and a portion of the heating medium to the liquid zone of the vessel;
   partially vaporizing volatile components of the process stream by thermal exchange with the heating medium in the liquid zone;
   removing a vaporized portion of the process stream from a vapor zone of the vessel;
   moving solids from the process stream to the heating medium in the liquid zone; and
   removing solids from the heating medium.

2. A method according to claim 1 wherein providing the mixture of the process stream and the portion of the heating medium to the liquid zone of the vessel comprises mixing the process stream and the portion of the heating medium wherein no vaporization of the volatile components of the process stream occurs.

3. A method according to claim 1 wherein providing the mixture of the process stream and the portion of the heating medium to the liquid zone of the vessel comprises mixing the process stream and the portion of the heating medium wherein no more than about 90% of the volatile components of the process stream vaporize.

4. A method according to claim 1 further comprising separating and removing at least some of the solids from the heating medium directly as blowdown containing the at least some of the solids.

5. A method according to claim 1 further comprising:
   removing a portion of the heating medium;
   raising a temperature of the removed portion to produce a heated recycle stream; and
   routing the heated recycle stream back to the liquid zone.

6. A method according to claim 5 wherein the removed portion of the heating medium is a mixture of heating medium and at least some of the solids of the process stream.

7. A method according to claim 6 further comprising separating and removing at least some of the solids from the removed portion prior to raising the temperature.

8. A method according to claim 1 further comprising condensing at least a portion of the vaporized process stream.

9. A method according to claim 1 further comprising compressing at least a portion of the vaporized process stream.

10. A method according to claim 1 further comprising raising a temperature of at least a portion of the process stream prior to the process stream directly entering the liquid zone of the vessel.

11. A method according to claim 1 wherein a density of the heating medium is greater than that of the process stream.

12. A method according to claim 1 wherein the process stream includes water.

13. A system to partially vaporize a process stream, the system comprising:
- a vessel arranged to receive the process stream into a liquid zone of the vessel, the liquid zone comprising a heating medium less volatile than the process stream, immiscible with the process stream, and maintained at a vaporization operating temperature;
- a pre-mixer fluidly coupled to the liquid zone of the vessel and arranged to mix the process stream and a portion of the heating medium remote from the liquid zone; and
- a pump-around loop arranged to remove a portion of the heating medium from the liquid zone and return the portion back to the liquid zone; a separation device disposed within said pump-around loop;
- wherein volatile components of the process stream partially vaporize by thermal exchange with the heating medium and migrate to a vapor zone of the vessel for removal, and solids move from the process stream and collect in the heating medium.

14. A system according to claim 13 wherein the mixer is arranged so no more than about 90% of the volatile components of the process stream vaporize in the mixer.

15. A system according to claim 13 wherein the vessel includes internals arranged to separate at least some of an unvaporized portion of the process stream from the heating medium.

16. A system according to claim 13 wherein the pump-around loop includes a heater.

17. A system according to claim 13 further comprising a condenser arranged to receive at least a portion of a vaporized process stream exiting the vapor zone of the vessel.

18. A system according to claim 13 further comprising a compressor arranged to receive at least a portion of a vaporized process stream exiting the vapor zone of the vessel and produce a pressurized vaporized process stream.

* * * * *